(12) United States Patent
Hong

(10) Patent No.: US 8,945,844 B2
(45) Date of Patent: Feb. 3, 2015

(54) METHOD OF AMPLIFYING TARGET NUCLEIC ACID WITH REDUCED AMPLIFICATION BIAS AND METHOD FOR DETERMINING RELATIVE AMOUNT OF TARGET NUCLEIC ACID IN SAMPLE

(75) Inventor: Sung-woo Hong, Gwangmyeong-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 190 days.

(21) Appl. No.: 13/546,850

(22) Filed: Jul. 11, 2012

(65) Prior Publication Data

US 2013/0017549 A1    Jan. 17, 2013

(30) Foreign Application Priority Data

Jul. 11, 2011   (KR) .................. 10-2011-0068556
May 10, 2012   (KR) .................. 10-2012-0049776

(51) Int. Cl.
*C12Q 1/68* (2006.01)
*C12P 19/34* (2006.01)

(52) U.S. Cl.
CPC .................... *C12Q 1/6851* (2013.01)
USPC ............. 435/6.12; 435/6.1; 435/6.11

(58) Field of Classification Search
None
See application file for complete search history.

(56) References Cited

U.S. PATENT DOCUMENTS 7,575,863 B2    8/2009    Chen et al.
2003/0148340 A1 *  8/2003    Harney et al. .............. 435/6

2010/0062494 A1    3/2010    Church et al.
2010/0279305 A1    11/2010   Kuersten
2010/0297630 A1 *  11/2010   Reijans et al. ............. 435/6

FOREIGN PATENT DOCUMENTS

WO    2006/111784 A1    10/2006
WO    2010/120803 A2    10/2010

OTHER PUBLICATIONS

Shi et al., "Facile Means for Quantifying MicroRNA Expression by Real-Time PCR," *BioTechniques*, Oct. 2005, 519-525, 39-4, Informa.
Benes et al., "Expression Profiling of MicroRNA Using Real-Time Quantitative PCR, How to Use it and What is Available," *Methods*, 2010, 244-249, 50-4, Elsevier Inc.
Cheng et al., "Highly Sensitive Determination of MicroRNA Using Target-Primed and Branched Rolling-Circle Amplification," *Angewandte Chemie*, 2009, 3318-3322, 121, Wiley-VCH Verlag GmbH & Co. KGaA, Weinheim, Germany.
Klevebring et al., "Genome-Wide Profiling of Populus Small RNAs," *BMC Genomics*, 10(1): 620-638 (2009).
Takada et al., "Profiling of MicroRNA Expression by mRAP," *Protocol*, 2(12): 3136-3145 (2007).
Ho et al., "A Simplified Method for Cloning of Short Interfering RNAs from *Brassica juncea* Infected with *Turnip mosaic potyvirus* and *Turnip crinkle carmovirus*," *J. of Virological Methods*, 136: 217-223 (2006).
Margulies et al., "Genome Sequencing in Microfabricated High-Density Picolitre Reactors," *Nature*, 437(7057): 376-380 (2005).
Chappell et al., "Isolation and Cloning of Small RNAs from Virus-Infected Plants," *Current Protocol in Microbiology*, 16H.2.1-16H.2.17 (2005).
Extended European Search Report by the European Patent Office in International Application No. 12175902.1, mailed on Sep. 10, 2012.

* cited by examiner

*Primary Examiner* — Young J Kim
(74) *Attorney, Agent, or Firm* — Leydig, Voit & Meyer, Ltd.

(57) ABSTRACT

A method of amplifying a target nucleic acid with reduced amplification bias and a method of determining a relative amount of a target nucleic acid in a sample.

19 Claims, 1 Drawing Sheet

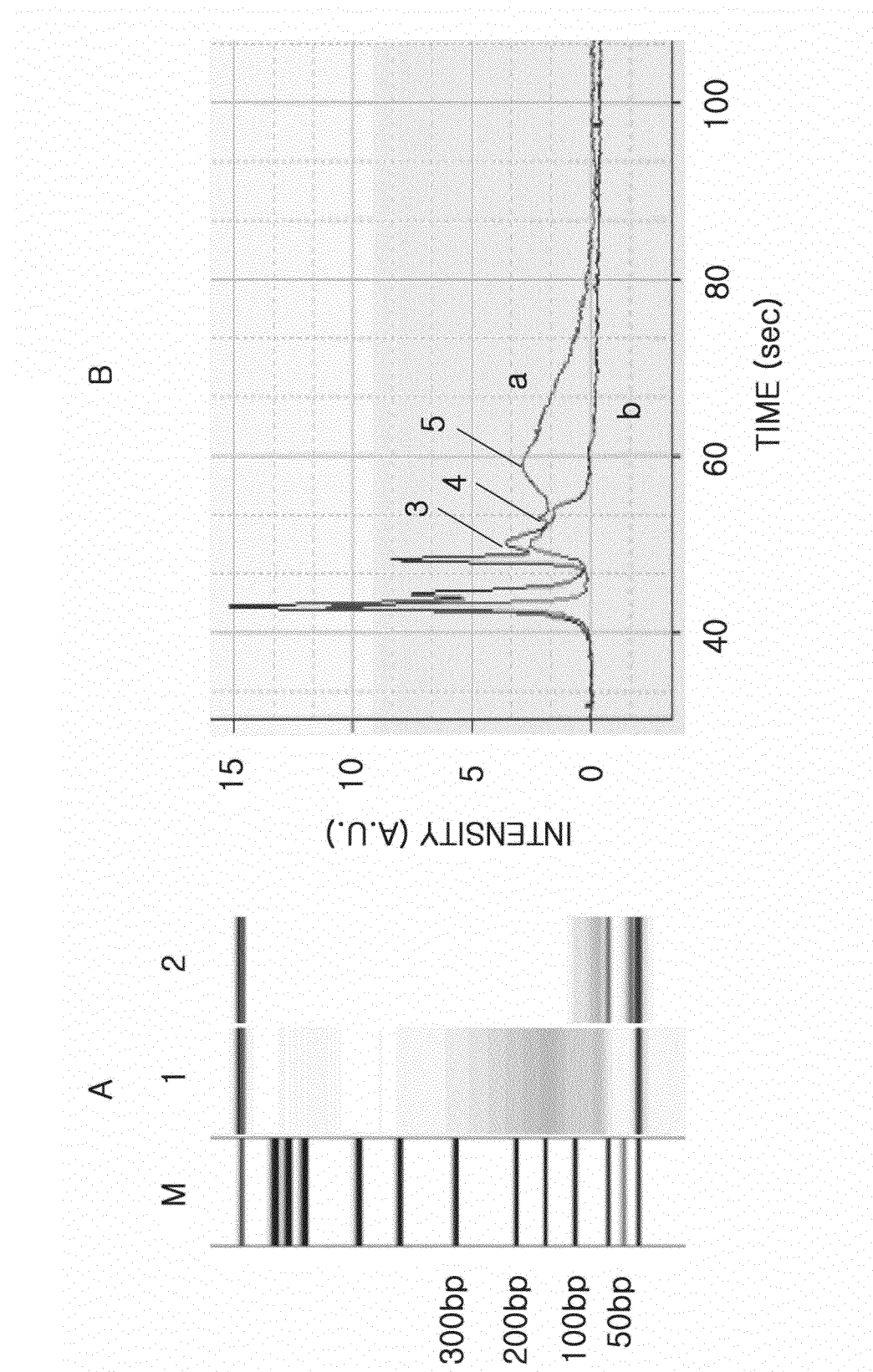

SEQUENCE LISTING

<160> NUMBER OF SEQ ID NOS: 24

<210> SEQ ID NO 1
<211> LENGTH: 22
<212> TYPE: RNA
<213> ORGANISM: Homo sapiens

<400> SEQUENCE: 1
uucaacgggu auuuauugag ca                                                  22

<210> SEQ ID NO 2
<211> LENGTH: 23
<212> TYPE: RNA
<213> ORGANISM: Homo sapiens

<400> SEQUENCE: 2
uggaagacua gugauuuugu ugu                                                 23

<210> SEQ ID NO 3
<211> LENGTH: 22
<212> TYPE: RNA
<213> ORGANISM: Homo sapiens

<400> SEQUENCE: 3
uggaauguaa agaaguaugu au                                                  22

<210> SEQ ID NO 4
<211> LENGTH: 23
<212> TYPE: RNA
<213> ORGANISM: Homo sapiens

<400> SEQUENCE: 4
ucuuugguua ucuagcugua uga                                                 23

<210> SEQ ID NO 5
<211> LENGTH: 22
<212> TYPE: RNA
<213> ORGANISM: Homo sapiens

<400> SEQUENCE: 5
uagcagcacg uaaauauugg cg                                                  22

<210> SEQ ID NO 6
<211> LENGTH: 23
<212> TYPE: RNA
<213> ORGANISM: Homo sapiens

<400> SEQUENCE: 6
caaagugcuu acagugcagg uag                                                 23

<210> SEQ ID NO 7
<211> LENGTH: 22
<212> TYPE: RNA
<213> ORGANISM: Homo sapiens

<400> SEQUENCE: 7
cauugcacuu gucucggucu ga                                                  22

<210> SEQ ID NO 8
<211> LENGTH: 21
<212> TYPE: RNA
<213> ORGANISM: Homo sapiens

<400> SEQUENCE: 8
aggcaagaug cuggcauagc u                                              21

<210> SEQ ID NO 9
<211> LENGTH: 21
<212> TYPE: RNA
<213> ORGANISM: Homo sapiens

<400> SEQUENCE: 9
cccggagcca ggaugcagcu c                                              21

<210> SEQ ID NO 10
<211> LENGTH: 22
<212> TYPE: RNA
<213> ORGANISM: Homo sapiens

<400> SEQUENCE: 10
acucggcgug gcgucggucg ug                                             22

<210> SEQ ID NO 11
<211> LENGTH: 19
<212> TYPE: RNA
<213> ORGANISM: Homo sapiens

<400> SEQUENCE: 11
gagggcgggu ggaggagga                                                 19

<210> SEQ ID NO 12
<211> LENGTH: 20
<212> TYPE: RNA
<213> ORGANISM: Homo sapiens

<400> SEQUENCE: 12
ccccagggcg acgcggcggg                                                20

<210> SEQ ID NO 13
<211> LENGTH: 19
<212> TYPE: RNA
<213> ORGANISM: Homo sapiens

<400> SEQUENCE: 13
ggggccuggc ggugggcgg                                                 19

<210> SEQ ID NO 14
<211> LENGTH: 18
<212> TYPE: RNA
<213> ORGANISM: Homo sapiens

<400> SEQUENCE: 14
cggggcggca ggggccuc                                                  18

<210> SEQ ID NO 15
<211> LENGTH: 18
<212> TYPE: RNA
<213> ORGANISM: Homo sapiens

<400> SEQUENCE: 15
agcaggugcg gggcggcg                                                  18

<210> SEQ ID NO 16
<211> LENGTH: 23
<212> TYPE: DNA
<213> ORGANISM: Artificial Sequence
<220> FEATURE:

```
<223> OTHER INFORMATION: P5-A5: 5' terminal primer-5' terminal adapter
      sequence

<400> SEQUENCE: 16
tgagttctac ggtacctcta agc                                          23

<210> SEQ ID NO 17
<211> LENGTH: 24
<212> TYPE: DNA
<213> ORGANISM: Artificial Sequence
<220> FEATURE:
<223> OTHER INFORMATION: A3-P3: 3' terminal adaper-3' terminal primer
      sequence

<400> SEQUENCE: 17
aggcataagc tgttagctca gaat                                         24

<210> SEQ ID NO 18
<211> LENGTH: 24
<212> TYPE: DNA
<213> ORGANISM: Artificial Sequence
<220> FEATURE:
<223> OTHER INFORMATION: reverse primer : sequence complementary to
      P3-A3 sequence

<400> SEQUENCE: 18
attctgagct aacagcttat gcct                                         24

<210> SEQ ID NO 19
<211> LENGTH: 19
<212> TYPE: RNA
<213> ORGANISM: Homo sapiens

<400> SEQUENCE: 19
gggggaagaa aaggugggg                                               19

<210> SEQ ID NO 20
<211> LENGTH: 26
<212> TYPE: RNA
<213> ORGANISM: Artificial Sequence
<220> FEATURE:
<223> OTHER INFORMATION: P5-A5: primer or primer binding sequence
      linked to 5 terminus adaptor sequence

<400> SEQUENCE: 20
cggugagguc uuugguucau cgaucg                                       26

<210> SEQ ID NO 21
<211> LENGTH: 26
<212> TYPE: RNA
<213> ORGANISM: Artificial Sequence
<220> FEATURE:
<223> OTHER INFORMATION: A3-P3: 3 terminus adaptor sequence linked to a
      primer or a primer binding sequence

<400> SEQUENCE: 21
cgaucguguc cucaaggcua ccaccu                                       26

<210> SEQ ID NO 22
<211> LENGTH: 15
<212> TYPE: DNA
<213> ORGANISM: Artificial Sequence
<220> FEATURE:
<223> OTHER INFORMATION: reverse transcription primer

<400> SEQUENCE: 22
```

-continued

```
atcgcgagaa ttcca                                                    15

<210> SEQ ID NO 23
<211> LENGTH: 20
<212> TYPE: DNA
<213> ORGANISM: Artificial Sequence
<220> FEATURE:
<223> OTHER INFORMATION: forward primer

<400> SEQUENCE: 23
cggtgaggtc tttggttcat                                               20

<210> SEQ ID NO 24
<211> LENGTH: 20
<212> TYPE: DNA
<213> ORGANISM: Artificial Sequence
<220> FEATURE:
<223> OTHER INFORMATION: reverse primer

<400> SEQUENCE: 24
aggtggtagc cttgaggaca                                               20
```

METHOD OF AMPLIFYING TARGET NUCLEIC ACID WITH REDUCED AMPLIFICATION BIAS AND METHOD FOR DETERMINING RELATIVE AMOUNT OF TARGET NUCLEIC ACID IN SAMPLE

CROSS-REFERENCE TO RELATED APPLICATIONS

This application claims the benefit of Korean Patent Application No. 10-2011-0068556, filed on Jul. 11, 2011, and Korean Patent Application No. 10-2012-0049776, filed on May 10, 2012, in the Korean Intellectual Property Office, the entire disclosures of which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,534 Byte ASCII (Text) file named "710693_ST25.txt," created on Jul. 11, 2012.

BACKGROUND

1. Field

The present disclosure relates to methods of amplifying a target nucleic acid and methods of determining a relative amount of a target nucleic acid in a sample.

2. Description of the Related Art

Nucleic acid amplification refers to an increase in the number of copies of a target nucleic acid sequence or its complementary sequence. Nucleic acid amplification is well known in the art. The amplification of a nucleic acid includes methods that require multiple cycles during the amplification process, and methods that are performed at a single temperature. Cycling techniques are exemplified by methods requiring thermo-cycling, such as polymerase chain reaction (PCR). PCR generally involves thermally denaturing a double-stranded DNA to provide single stranded DNAs, annealing a primer to the single stranded DNA; and synthesizing a complementary strand from the primer.

Isothermal amplification is an amplification process performed at a single temperature, or wherein the major aspect of the amplification process is performed at a single temperature. In the PCR process, the product of the reaction is heated to separate the two strands of DNA such that a primer may bind to the template strand. Conversely, the isothermal techniques rely on a strand displacing polymerase in order to separate the two strands of a double strand and re-copy the template. Isothermal techniques may be classified into methods that rely on the replacement of a primer to initiate a reiterative template copying, and those that rely on continued re-use or new synthesis of a single primer molecule. The methods that rely on the replacement of the primer include helicase dependant amplification (HDA), exonuclease dependant amplification, recombinase polymerase amplification (RPA), and loop mediated amplification (LAMP). The methods that rely on continued re-use or new synthesis of a single primer molecule include strand displacement amplification (SDA) or nucleic acid based amplification (NASBA and TMA).

The above methods can be used to amplify short nucleic acid sequences, such as microRNAs (miRNAs). However, an amplification bias often is generated, which will vary according to the number of copies of the target nucleic acid and relative abundance of certain nucleotides, for example, AT content or GC content. For example, when each of microRNAs (miRNAs) is amplified in a sample including a plurality of miRNAs, i.e., in a sample including a miRNA library, the amplification bias may vary according to the sequence of the miRNAs and the number of copies of the miRNAs present in the sample. In general, miRNA has a length in the range of about 18 to 25 nucleotides (nt) and about 21 to 24 nt on average and has more than 1000 types of sequences.

Thus, there is still a need to develop a method of amplifying a plurality of target nucleic acids, particularly short nucleic acid sequences such as an miRNA library, without amplification bias or with reduced amplification bias.

SUMMARY

Provided is a method of simultaneously amplifying a plurality of target nucleic acids, which method comprises ligating two or more different target nucleic acids to provide a ligated product, and amplifying the ligated product.

Also provided is a method of determining the relative amount of a target nucleic acid contained in a sample that contains a plurality of nucleic acids, the method comprising simultaneously amplifying the plurality of nucleic acids as described herein, and determining the amount of the amplified target nucleic acid relative to the other amplified nucleic acids, wherein the relative amount of the amplified target nucleic acid reflects the relative amount of the target nucleic acid contained in the sample.

These and/or other aspects will become apparent and more readily appreciated from the following drawings and detailed description of the invention.

BRIEF DESCRIPTION OF THE DRAWINGS

FIGS. 1A and 1B show electrophoresis results of amplified products. FIG. 1A is a photograph of electrophoresis, and FIG. 1B is an electropherogram of FIG. 1A.

DETAILED DESCRIPTION

Reference will now be made in detail to embodiments including the accompanying drawings. Descriptions of the various embodiments are for purposes of illustrating the invention, and should not be construed as limiting excepted as expressly noted. Expressions such as "at least one of," when preceding a list of elements, modify the entire list of elements and do not modify the individual elements of the list.

According to an embodiment of the present invention, there is provided a method of simultaneously amplifying a plurality of target nucleic acids, the method comprising ligating two or more different target nucleic acids to provide a ligated product and amplifying the ligated product. Target nucleic acid refers to any nucleic acid that is a desired target for amplification. Thus, the target nucleic acid can be a particular DNA or RNA sequence of interest, including the complimentary sequence thereof. In describing the invention, the term "target sequence" or "target nucleic acid sequence" also is referred to herein. This term refers to the sequence of the target nucleic acid to be amplified, or the complimentary sequence thereof, which may be distinct from other nucleic acid sequences contained in a larger nucleic acid construct.

The plurality of nucleic acids can be provided by a sample including a plurality of different target nucleic acids. The sample may be any sample including the target nucleic acids. For example, the sample may include a biological sample or a chemical sample which includes the target nucleic acids.

The biological sample which is derived from a living organism may be directly isolated from the living organism, or isolated and further processed, for example, by using purification and amplification. Biological samples include, for instance, body fluids (e.g., blood, urine, saliva, lymph), tissue, and cells, and biological samples that have been further processed, including serum, nucleic acids isolated from the living organism, or amplified nucleic acids. The chemical sample may include chemically synthesized target nucleic acids. The nucleic acid can be RNA or DNA, including miRNA. The term "miRNA" may be a short RNA found in eukaryotic cells. The miRNA has important functions in cell physiology and may act as a controller after translation of gene expression. The miRNA may be isolated by a method using a TRizol/TRI-reagent. The miRNA may also be isolated by using a known isolation kit, for example, an mirVana isolation kit (Ambion) and an RNeasy kit (Qiagen).

The target nucleic acid may have a length of about 200 nt or less (e.g., about 150 nt or less, 125 nt or less, 100 nt or less, 75 nt or less, 50 nt or less, etc.). The target nucleic generally will have a length of about 15 nt or more (e.g., 18 nt or more, or 25 nt or more). For example, the length of the target nucleic acids may be in the range of about 15 to about 200 nt, about 15 to about 170 nt, about 15 to about 150 nt, about 15 to about 120 nt, about 15 to about 100 nt, about 15 to about 80 nt, about 15 to about 75 nt, about 15 to about 70 nt, about 18 to about 200 nt, about 18 to about 170 nt, about 18 to about 150 nt, about 18 to about 120 nt, about 18 to about 100 nt, about 18 to about 80 nt, about 18 to about 75 nt, about 18 to about 70 nt, about 18 to about 50 nt, about 18 to about 30 nt, about 18 to about 27 nt, about 8 to about 25 nt, about 18 to about 25 nt, about 20 to about 70 nt, or about 21 to about 25 nt. For example, the target nucleic acid may have a length corresponding to that of a pre-miRNA or a miRNA. Examples of RNA targets include, for instance, tRNA, rRNA, mRNA, and miRNA. Examples of DNA targets include genomic DNA fragments and cDNA prepared from RNA.

The term "plurality of target nucleic acids" used herein indicates that at least two (two or more) nucleic acid molecules having different sequences are contained in one sample. For example, a sample containing at least two miRNA molecules having different sequences is said to contain "a plurality of target nucleic acids." The term "at least two" includes the boundaries of at least three, at least four, at least five, at least n (n being an arbitrary integer of higher than 6), as well as an arbitrary specific number of types of target nucleic acid being an integer of two or higher, e.g. 2, 3, 4, 5, 6, 7, 8, 9, 10, 11, 12, 13, 14, 15, m (m being an arbitrary integer of higher than 16), all of which are enclosed herewith.

The method includes ligating two or more different target nucleic acids to provide a ligated product. The ligating may be performed by using any method known in the art. For example, the ligating may be performed in the presence of at least one of an RNA ligase or DNA ligase. Conditions for the ligating the target nucleic acids in the presence of at least one of the RNA ligase or DNA ligase are well known in the art. For example, the conditions for the ligating may include a solution that includes a nucleic acid having a phosphorylated 5'-P-terminal, a nucleic acid having a 3'-hydroxyl-terminal, and ATP. For example, the RNA ligase may include a T4 RNA ligase 1 or 2. The DNA ligase may include a T4 DNA ligase. The reaction may be conducted in a buffer suitable for the ligation. The reaction temperature may be in the range of about 35° C. to about 40° C., for example, about 37° C.

The ligating is performed by mediating ligation with an adaptor sequence (inserting or introducing an adaptor sequence between the target nucleic acids). The ligating may be performed by ligating one target nucleic acid having a 3'-terminal to which a 3'-terminal-specific adaptor sequence is bound to another target nucleic acid having a 5'-terminal to which a 5'-terminal-specific adaptor sequence is bound. The term "adaptor sequence" refers to a nucleic acid sequence for the ligation to the 3'-terminal or the 5'-terminal of the target nucleic acid. The adaptor sequence may be DNA or RNA. The adaptor sequence may be a single stranded sequence or a double stranded sequence. The adaptor sequence may have a GC content in the range of about 20% to about 80%, for example, about 30% to about 80%, about 40% to about 80%, about 50% to about 80%, about 60% to about 80%, about 70% to about 80%, about 60% to about 70%, about 30% to about 70%, about 30% to about 60%, about 30% to about 50%, about 30% to about 40%, about 40% to about 50%, or about 40% to about 70%. The adaptor sequence may have a length in the range of about 3 nt to about 100 nt. The length of the adaptor sequence may be in the range of about 3 nt to about 70 nt, about 3 nt to about 50 nt, about 3 nt to about 30 nt, about 3 nt to about 20 nt, about 3 nt to about 10 nt, about 3 nt to about 7 nt, about 4 nt to about 20 nt, about 4 nt to about 10 nt, or about 4 nt to about 7 nt.

The term "adaptor sequence specific to the 3'-terminal" or "adaptor sequence specific to the 5'-terminal" refers to adaptor sequences that specifically bind to the 3'-terminal and 5'-terminal of the target nucleic acid, respectively.

The ligating may be conducted by selectively blocking or activating the reactivity of the 5'-terminal and the 3'-terminal of the target nucleic acid and the adaptor sequence. For example, a 5'-terminal adaptor sequence may be ligated only to the 5'-terminal of the target nucleic acid, e.g., miRNA or cDNA thereof, by phosphorylating the 5'-terminal of the target nucleic acid, blocking the 3'-terminal of the target nucleic acid, for example, by converting the 3'-terminal-OH group into a phosphoryl group, and reacting the 5'-terminal adaptor sequence (A5) having a 3'-terminal-OH group in the presence of a DNA or RNA ligase. In this regard, the 5'-terminus of the 5'-terminal adaptor sequence may be selectively phosphorylated. The 3'-terminal adaptor sequence (A3) may be ligated only to the 3'-terminal of the ligated product by reacting the ligated product with the 3'-terminal adaptor sequence having a phosphorylated 5'-terminal in the presence of a DNA or RNA ligase. In this regard, the 3'-terminal of the 3'-terminal adaptor sequence may be selectively phosphorylated. The adaptor sequence specific to the 3'-terminal and the 5'-terminal of the target nucleic acid may be introduced sequentially to the 5'-terminal and the 3'-terminal of the target nucleic acid, or sequentially to the 3'-terminal and then the 5'-terminal of the target nucleic acid, or simultaneously to the 5'-terminal and the 3'-terminal of the target nucleic acid. The 5'-terminal-specific adaptor sequence and the 3'-terminal-specific adaptor sequence may have the same nucleotide sequence or different nucleotide sequences.

An example of simultaneously introducing the adaptor sequences to the 5'-terminal and the 3'-terminal is as follows. A target nucleic acid having a phosphorylated 5'-terminal and a 3'-terminal OH group, a 5'-terminal adaptor sequence having a non-phosphorylated 5'-terminal and a 3'-terminal OH group, and a 3'-terminal adaptor sequence having a phosphorylated 5'-terminal and a blocked 3'-terminal are reacted in the presence of a DNA or RNA ligase, so that the adaptor sequences respectively specific to the 5'-terminal and the 3'-terminal of the target nucleic acid may be bonded to the 5'-terminal and the 3'-terminal of the target nucleic acid.

The two or more target nucleic acids, thus, may include at least one target nucleic acid comprising a 3'-terminal adaptor sequence, and at least one target nucleic acid comprising a 5'-terminal adaptor sequence. The two or more target nucleic acids have an adaptor sequence at least at the 5' or 3' terminus thereof, but may have adaptor sequences at both the 5' and 3' terminus. The two nucleic acids having the specific adaptor sequence at least at one of the 5'-terminal or the 3'-terminal thereof may be ligated to each other.

The target nucleic acids may further comprise a primer or primer binding sequence ligated to the 3' or 5' terminus of the ligated product (e.g., ligated to the 5' or 3' adaptor sequence). Thus, in one embodiment, the method includes ligating a primer sequence or a primer-binding sequence to at least one of the 3'-terminal and the 5'-terminal of the ligated product of the target nucleic acids (at least one of the 3'-terminal or 5'-terminal adaptor sequences of the ligated product). The primer sequence or the primer-binding sequence may be ligated to the 3'-terminal or the 5'-terminal of the ligated product in the same manner as the ligation between the adaptor sequence and the target nucleic acid. At least one of the primer sequence and the primer-binding sequence may be specifically ligated to one of the 3'-terminal and the 5'-terminal.

The primer sequence or primer binding sequence can be pre-ligated to an adaptor sequence (i.e., prior to ligating the adaptor sequence to the target nucleic acid). Thus, for instance, a pre-ligated primer-adaptor sequence can be added to the 3'- or 5'-terminus of a target nucleic acid, thereby adding the primer and adaptor sequences in a single step. In one embodiment, an end-blocked primer-adapter sequence is used, such that the primer cannot be ligated in subsequent reactions and ensuring that the primer sequence resides at the 3' or 5' terminus of the ligated product as desired. For example, the two or more target nucleic acids may be ligated to a primer-adaptor sequence by combining the two or more different target nucleic acids with one or more pre-ligated, end-blocked 3'-primer-adapter sequences, or one or more pre-ligated, end-blocked 5'-primer-adapter sequences.

In some embodiments, the adapter sequence or portion thereof can serve as the primer or primer binding sequence, in which case ligating a primer sequence or a primer-binding sequence to at least one of the 3'-terminal or the 5'-terminal of the ligated product of the target nucleic acids is not necessary. The adaptor sequence may be used as a primer sequence or primer binding sequence. For example, when the ligated product includes adaptors only at the 3'-terminal and/or the 5'-terminal of the ligated product of the target nucleic acids, the method does not necessarily include ligating a primer sequence or a primer-binding sequence to at least one of the 3'-terminal or the 5'-terminal of the ligated product of the target nucleic acids.

The term "primer-binding sequence" refers to a sequence complementary to the primer to be used. The term "primer sequence" refers to a nucleic acid sequence that functions as a starting point of polymerization of a nucleic acid. The primer sequence or primer binding sequence may bind to the target nucleic acid (or ligated product of the target nucleic acid(s) and adapter sequences) and have a 3'-OH group. The primer or primer binding sequence may be DNA or RNA. The primer or primer binding sequence may be a single strand. The primer sequence may have a GC content in the range of about 20% to about 80%, for example, about 30% to about 80%, about 40% to about 80%, about 50% to about 80%, about 60% to about 80%, about 70% to about 80%, about 60% to about 70%, about 30% to about 70%, about 30% to about 60%, about 30% to about 50%, about 30% to about 40%, about 40% to about 50%, or about 40% to about 70%. The primer sequence may have a length in the range of about 10 nt to about 100 nt. For example, the length of the primer sequence may be in the range of about 10 nt to about 70 nt, about 10 nt to about 50 nt, about 10 nt to about 30 nt, about 10 nt to about 20 nt, about 15 nt to about 100 nt, about 15 nt to about 70 nt, about 15 nt to about 50 nt, about 15 nt to about 40 nt, or about 15 nt to about 30 nt.

The primer sequence or primer binding sequence can be pre-ligated to an adaptor sequence. The two or more target nucleic acids may comprise combining two or more different target nucleic acids with one or more pre-ligated, end-blocked 3'-primer-adapter sequences, or one or more pre-ligated, end-blocked 5'-primer-adapter sequences.

As is apparent from the foregoing description, the adaptor and primer sequences can be added to the target nucleic acids in a variety of different ways. For instance, an adaptor sequence (e.g., a end-blocked adaptor sequence) may be ligated to the 3' terminus of two or more target nucleic acids, and the target nucleic acids subsequently ligated to one another (with a step of removing the end-block from the adaptor, if needed) to provide a ligated product having a structure: (target)-A3-((target)-A3]$_n$-(target)-A3, wherein A3 is the 3' adaptor sequence, (target) is the target nucleic acid sequence, and n is an integer representing the number of target nucleic acid sequences in the ligated product. The integer "n" may be in the range of 1,000 or less, for example 2-1,000, 2-800, 2-600, 2-500, 2-300, 2-200, or 2-100. Of course, the same process can be performed using a 5' adaptor sequence ligated to the 5' terminus of the target, in which case the ligated product would have the structure: A5-(target)-[A5-(target)]$_n$-A5-(target), wherein A5 is the 5' adaptor sequence. The primer or primer binding sequence(s) can be added to the 3' and/or 5' terminus of the ligated product, as desired, providing a ligated product having the structure:

P5-(target)-A3-((target)-A3]$_n$-(target)-A3;
P5-(target)-A3-((target)-A3]$_n$-(target)-A3-P3;
(target)-A3-((target)-A3]$_n$-(target)-A3-P3;
P5-A5-(target)-[A5-(target)]$_n$-A5-(target);
P5-A5-(target)-[A5-(target)]$_n$-A5-(target)-P3; or
A5-(target)-[A5-(target)]$_n$-A5-(target)-P3;

wherein P5 and P3 are the 5' and 3' primer or primer binding sequences, respectively, and each of A5, A3, (target), and n are as previously defined.

Alternatively, adaptor sequences can be added to both of the 3' and 5' termini of the target nucleic acids, and the target nucleic acids subsequently ligated to provide a ligated product having the structure: Of course, the same process can be performed using a 5' adaptor sequence ligated to the 5' terminus of the target, in which case the ligated product would have the structure: A5-(target)-A3-[A5-(target)-A3]$_n$-A5-(target)-A3, wherein each of A5, A3, (target), and n are as defined above. Primer and primer binding sequences can be added to the 3' and/or 5' termini to provide a ligated product having the structure:

P5-A5-(target)-A3-[A5-(target)-A3]$_n$-A5-(target)-A3;
A5-(target)-A3-[A5-(target)-A3]$_n$-A5-(target)-A3-P3; or
P5-A5-(target)-A3-[A5-(target)-A3]$_n$-A5-(target)-A3-P3;

wherein P5, P3, A5, A3, (target), and n are as previously defined.

The ligation of the adaptor and primer or primer binding sequences to the target nucleic acids, and the ligation of the target nucleic acids comprising the adaptor and/or primer or primer binding sequences can be performed in any suitable order, using end-blocking (protecting) groups as needed in order to obtain a ligated product with the desired structure, such as any of the ligated products referenced herein. Suitable protocols are illustrated by the Examples provided herein.

In a particular embodiment, no intervening adaptor sequences are used. Instead, the target nucleic acids are ligated to one another and a primer (or primer binding sequence) or adapter-primer (or adapter-primer binding sequence) is added to the 3' and/or 5' terminus, before, simultaneously, or after ligation of the target sequences to one another. By way of further illustration, an end-blocked adapter-primer sequence can be added to a mixture of target nucleic acids, and the mixture ligated to provide nucleic acids of varying lengths having the structure: (target)-(target)$_n$-(target)-A3-P3, wherein A3 is an adaptor sequence, P3 is an end-blocked primer or primer binding sequence, and target is a target sequence, and n is as previously defined. An adaptor-primer or adapter-primer binding sequence can then be added to the 5' terminus of the ligated product to provide a product having the structure: P5-A5-(target)-(target)$_n$-(target)-A3-P3. Of course, the process can be performed adding the P5-A5 group first by using a 5' adaptor-endblocked primer in the first step instead of the 3' adaptor-primer. By way of further illustration, when the end-blocked adapter-primer sequence, for example, 5'-hydroxyl 5' end blocked P5-A5 instead of 5'-phosphoryl and 3'-hydroxyl P5-A5 and/or 2',3'-dideoxy 3' end blocked A3-P3 is used as similar way as described above, the adaptor-primer sequence may be added to only 5',3' or both 5' and 3' terminal.

The method includes amplifying the ligated product. The term "amplifying" refers to an increase in the number of copies of the target nucleic acid and its complementary sequence. The amplification may be performed by using any method known in the art. The amplification of nucleic acid includes methods that require multiple cycles during the amplification process, and methods that are performed at a single temperature (isothermal). Cycling techniques are exemplified by methods requiring thermo-cycling. The methods requiring thermo-cycling include polymerase chain reaction (PCR), which is well known in the art. The PCR includes denaturing a double-stranded DNA into single stranded DNAs by thermal denaturation, annealing a primer to the single stranded DNAs; and synthesizing a complementary strand from the primer. Isothermal amplification is an amplification performed at a single temperature or where the major aspect of the amplification process is performed at a single temperature. In the PCR process, the product of the reaction is heated to separate the two strands such that another primer may bind to the template. Conversely, the isothermal techniques rely on a strand displacing polymerase in order to separate the two strands of a double strand and re-copy the template. Isothermal techniques may be classified into methods that rely on the replacement of a primer to initiate a reiterative template copying and those that rely on continued re-use or new synthesis of a single primer molecule. The methods that rely on the replacement of the primer include helicase dependant amplification (HDA), exonuclease dependant amplification, recombinase polymerase amplification (RPA), and loop mediated amplification (LAMP). The methods that rely on continued re-use or new synthesis of a single primer molecule include strand displacement amplification (SDA) or nucleic acid based amplification (NASBA and TMA).

The amplifying may be performed by amplifying the ligated product as a single amplification product (e.g., a single amplified amplicon). That is, the primer may be selected such that one amplified product includes all target nucleic acids contained in one ligated product. For example, in a PCR, a forward primer may be complementary to a 5'-terminal region of the most upstream target nucleic acid or an upstream region thereof, and a reverse primer may be complementary to a 3'-terminal region of the most downstream target nucleic acid or a downstream region thereof. The amplifying may be performed by using at least one of the sequence complementary to the primer sequence and the sequence complementary to the primer-binding sequence as a primer. According to one embodiment, the amplifying is performed by PCR, and forward and reverse primers are specifically annealed to a primer binding region of the ligated product that is separate from a target nucleic acid sequence. The ligated product may have a length of about 4,000 nt or less. For example, the length of the ligated product may be in the range of about 15 to about 4,000 nt, about 15 to about 3,500 nt, about 15 to about 3,000 nt, about 15 to about 3,000 nt, about 15 to about 2,500 nt, about 15 to about 2,000 nt, about 15 to about 1,500 nt, about 15 to about 1,000 nt, about 15 to about 800 nt, about 15 to about 600 nt, about 15 to about 400 nt, about 15 to about 200 nt, about 18 to about 4,000 nt, about 18 to about 3,500 nt, about 18 to about 3,000 nt, about 18 to about 3,000 nt, about 18 to about 2,500 nt, about 18 to about 2,000 nt, about 18 to about 1,500 nt, about 18 to about 1,000 nt, about 18 to about 800 nt, about 18 to about 600 nt, about 18 to about 400 nt, about 18 to about 200 nt, about 21 to about 4,000 nt, about 21 to about 2,000 nt, or about 21 to about 1,000 nt.

The primer can have any suitable sequence, but should not have a sequence complementary to any target nucleic acid sequence (e.g., sequence of a target miRNA or cDNA thereof) contained in the ligated product (e.g., miRNA or cDNA thereof). In a PCR, the forward primer is complementary to region of the ligated product that is upstream (5') of the target nucleic acid sequence. Thus, the forward primer should not have a sequence the same as the target nucleic acid sequence or a sequence complementary to the target nucleic acid. Similarly, the reverse primer is complementary to a region of the ligated product that is downstream (3') of the target nucleic acid. Accordingly, the reverse primer does not have a sequence that is the same as the target nucleic acid sequence or a sequence complementary to the target nucleic acid sequence. In this respect, the target nucleic acid sequence is the sequence of the target nucleic acid prior to ligation to any adaptor or primer sequences, one or more of which is contained in the ligated product.

The methods described herein can be used to amplify RNA or DNA targets. When the target nucleic acids to be amplified are RNAs, the method may further comprise, the method may further include producing a DNA (cDNA) complementary to the target nucleic acid by reverse-transcribing the target nucleic acid. If the target nucleic acid is RNA, the reverse-transcribing may be performed before or after ligated the target nucleic acid sequence to one or more adaptor or primer (or primer binding) sequences and to one another to provide the ligated product. It is known in the art that the reverse-transcribing produces a DNA complementary strand using an RNA strand using a reverse transcriptase.

Thus, the method may further include ligating an adaptor sequence to at least one of the 3'-terminal and the 5'-terminal of the target RNA before reverse-transcribing the RNA, such that the resulting RNA ligation product or cDNA thereof contains a sequence complimentary to the target RNA (the target nucleic acid sequence) and a sequence complimentary to the adaptor sequence, which complimentary sequence also is an adaptor sequence. The adaptor sequence may be specifically ligated to at least one of the 3'-terminal and the 5'-terminal of the target nucleic acid.

Alternatively, the method may include reverse transcribing a target RNA, and subsequently ligating one or more adaptor and primer (or primer binding) sequences to at least one of the 3'-terminal and the 5'-terminal of cDNA of the target nucleic acid after the reverse-transcribing. The adaptor sequence may be specifically ligated to at least one of the 3'-terminal and the 5'-terminal of the target nucleic acid. The ligating the adaptor sequence is as described above.

As previously discussed, each of the adaptor and primer sequences are, in some embodiments, selected so as to have a GC content of about 20-80%. In a related embodiment, the adaptor and primer sequences are selected such that the overall GC content of the ligated product, including primer (or primer binding) and adaptor sequences and the target nucleic acid sequences, is about 20-80%, for example, about 30% to about 80%, about 40% to about 80%, about 50% to about 80%, about 60% to about 80%, about 70% to about 80%, about 60% to about 70%, about 30% to about 70%, about 30% to about 60%, about 30% to about 50%, about 30% to about 40%, about 40% to about 50%, or about 40% to about 70%.

The ligated product, including primer (or primer binding) and adaptor sequences and the multiple target nucleic acid sequences, will typically be substantially larger than any single target nucleic acid in a sample. According to some embodiments, the ligated product may have a length of about 4,000 nt or less. For example, the length of the ligated produce may be in the range of about 15 to about 4,000 nt, about 15 to about 3,500 nt, about 15 to about 3,000 nt, about 15 to about 3,000 nt, about 15 to about 2,500 nt, about 15 to about 2,000 nt, about 15 to about 1,500 nt, about 15 to about 1,000 nt, about 15 to about 800 nt, about 15 to about 600 nt, about 15 to about 400 nt, about 15 to about 200 nt, about 18 to about 4,000 nt, about 18 to about 3,500 nt, about 18 to about 3,000 nt, about 18 to about 3,000 nt, about 18 to about 2,500 nt, about 18 to about 2,000 nt, about 18 to about 1,500 nt, about 18 to about 1,000 nt, about 18 to about 800 nt, about 18 to about 600 nt, about 18 to about 400 nt, about 18 to about 200 nt, about 21 to about 4,000 nt, about 21 to about 2,000 nt, or about 21 to about 1,000 nt.

According to another embodiment of the present invention, there is provided a method of determining a relative amount of a target nucleic acid in a sample, the method comprising amplifying two or more target nucleic acids contained in the sample according to the method described above; measuring an amount of the target nucleic acid from the amplified product; and determining a relative amount of the target nucleic acid in the sample by using the measured amount.

The amount of the target nucleic acid may be measured according to the amplified product by using any method known in the art. For example, the amount of the target nucleic acid may be measured by using a real time amplification. The real time amplification includes a Taqman™ method that uses a fluorescent dye and a fluorescent quencher and a method that uses a fluorescent material that binds to a double-stranded DNA. According to the Taqman™ method, the amount of the target nucleic acid may be measured in real time based on the amount of the fluorescent material detected during the amplification by using a Taqman™ probe that has a 5'-terminal to which a fluorescent reporter material is bound and a 3'-terminal to which a fluorescent quencher is bound, and includes a sequence specific to each of the target nucleic acids. During the amplification, as the primer is elongated by a DNA polymerase having a 5'←3' exonuclease activity and a new strand is synthesized, the probe annealed to the template is cleaved by the 5'←3' exonuclease activity. Because the probe is cleaved, the fluorescent dye is released. Accordingly, the fluorescent quencher is separated therefrom, and fluorescence increases. In this regard, the fluorescent reporter material may vary according to the target nucleic acid. Real time amplification using the Taqman™ probe is widely known in the art, and any know method may be used. In addition to real time amplification, the individual target nucleic acid may quantified or detected by using hybridization method using a specific probe for the individual target nucleic acid, and in this case the probe may be immobilized in a microarray. The individual target nucleic acid may quantified or detected by amplifying the individual target nucleic acid and detecting it by using a specific probe. For example, the detecting may be conducted by using a electrophoresis, or other detection method, for example, light, or electrical signal detection method. The quantified or detected amount can be used to calculate the relative amount of the individual target nucleic acid.

In the method that uses a fluorescent material that binds to a double-stranded DNA, a DNA-binding fluorescent material binds to all double-stranded DNAs during the PCR. During the PCR, an increase in the DNA products increases the intensity of fluorescence. The intensity is measured at each cycle, so that the concentration of DNA may be quantified. The DNA-binding fluorescent material may be SYBR Green I. The amount of the target nucleic acid may also be determined by using hybridization or electrophoresis of the amplified products.

The method includes determining a relative amount of the target nucleic acid in the sample by using the measured amount of the target nucleic acid. The determining the relative amount of the target nucleic acid may be performed by standardizing the amount of the target nucleic acid with respect to a predetermined value, for example, a threshold value, or comparing the amount of the target nucleic acid with a standard value.

The determined relative amount of the target nucleic acid may be used to determine relations between the target nucleic acid and various physiological conditions, for example, diseases.

According to the method of amplifying a target nucleic acid according to an embodiment, in a sample including a plurality of target nucleic acids, the target nucleic acid may be amplified with reduced amplification bias. Thus, a profile of the target nucleic acid in a sample may be more accurately determined from the amount of the amplified product.

For instance, when the methods described herein are used to amplify miRNA of a sample, multiple ligated products will be provided that will be different from one another and collectively represent the sequences of all of the miRNA targets of the sample. The relative abundance (copy number) of a given miRNA target will be represented by the number of copies of the target sequence (or complimentary sequence when using cDNA) in the ligated products. Amplification of the ligated products will, therefore, also provide a representative and proportional increase in the relative abundance (copy number) of the sequence in the amplified products. Information about the relative abundance (copy number) of the target sequences are then extracted from the amplified ligated product, for instance, by amplification by using specific primer for the individual target nucleic acid and detection of each of the individual target nucleic acid. The individual target nucleic acid may also quantified or detected by sequence analysis or hybridization based detection method. For example, a probe specific for the individual target nucleic acid immobilized on the substrate for example, on a microarray substrate and the amplified nucleic acid may be hybridized with the probe and the hybridization results may be detected, the detection results may indicated the amount of the individual target nucleic acid.

According to the method of determining a relative amount of a target nucleic acid in a sample according to another embodiment of the present invention, the relative amount of the target nucleic acid in the sample may be efficiently determined.

The present invention will be described in further detail with reference to the following examples. These examples are for illustrative purposes only and are not intended to limit the scope of the invention.

Example 1

Amplification of Target Nucleic Acid with Reduced Amplification Bias

1. Preparation of First Ligated Product in which Adaptor Sequence and Primer Sequence are Ligated to cDNA of Individual miRNA 15 types of miRNAs having different GC contents were selected as target nucleic acids to be amplified. A single strand DNA, which is cDNA of each miRNA, having a 3'-terminal and a 5'-terminal sequentially bound to an adaptor sequence and a primer sequence (first ligated product) was synthesized in order to mimick the ligated product having the 3'-terminal and the 5'-terminal sequentially bound to the adaptor sequence and the primer sequence.

In detail, a 3'-terminal adaptor sequence (A3) was ligated to the 3'-terminal of the cDNA of each miRNA, a 5'-terminal adaptor sequence (A5) was ligated to the 5'-terminal of the cDNA, a 3' primer sequence (P3) was ligated to the A3, and a 5' primer sequence (P5) was ligated to the A5, resulting in synthesizing the first ligated product (Bioneer Corporation, KOREA). The synthesized first ligated product has a general structure of P5-A5-cDNA of miRNA-A3-P3. In this regard, the P5 and the P3 are primer-binding sites. The P5-A5 and A3-P3 have sequences as follows.

P5-A5:
(SEQ ID NO: 16)
5'-TGAGTTCTACGGTACCTCTAAGC-3'

A3-P3:
(SEQ ID NO: 17)
5'-AGGCATAAGCTGTTAGCTCAGAAT-3'

As an amplification primer, a forward primer of the P5-A5 sequence (SEQ ID NO: 16), and a reverse primer complementary to the A3-P3 sequence which has 5'-ATTCTGAGCTAACAGCTTATGCCT-3' (SEQ ID NO: 18) was used.

Since the adaptor sequence and the primer sequence have the GC content in the range of 20% to 80%, the ligated product also has the GC content close to 20% to 80%.

The sequences of the 15 miRNAs are shown in Table 1 below.

TABLE 1

| No. | Name | SEQ ID NO: | GC content (%) | Tm (° C.) | Length (nt) |
|---|---|---|---|---|---|
| 1 | hsa-mir-95 | 1 | 36.4 | 60 | 22 |
| 2 | hsa-mir-7 | 2 | 34.8 | 62 | 23 |
| 3 | hsa-mir-1 | 3 | 27.3 | 56 | 22 |
| 4 | hsa-mir-9 | 4 | 34.8 | 62 | 23 |
| 5 | hsa-mir-16 | 5 | 45.5 | 64 | 22 |
| 6 | hsa-mir-17 | 6 | 47.8 | 68 | 23 |
| 7 | hsa-mir-25 | 7 | 50 | 66 | 22 |
| 8 | hsa-mir-31 | 8 | 52.4 | 64 | 21 |
| 9 | hsa-mir-1203 | 9 | 71.4 | 72 | 21 |
| 10 | hsa-mir-1307 | 10 | 72.7 | 76 | 22 |
| 11 | hsa-mir-3141 | 11 | 73.7 | 66 | 19 |
| 12 | hsa-mir-1915 | 12 | 90 | 76 | 20 |
| 13 | hsa-mir-2861 | 13 | 89.5 | 72 | 19 |

TABLE 1-continued

| No. | Name | SEQ ID NO: | GC content (%) | Tm (° C.) | Length (nt) |
|---|---|---|---|---|---|
| 14 | hsa-mir-3196 | 14 | 88.9 | 68 | 18 |
| 15 | hsa-mir-3665 | 15 | 83.3 | 66 | 18 |

2. Preparation of Second Ligated Product in which Adaptor Sequence and Primer Sequence are Ligated to cDNA of Individual miRNA 4 cDNAs selected from cDNAs complementary to SEQ ID NOS: 1 to 15 were ligated via adaptor sequences, and a primer sequence was ligated to both terminals of the ligated product to synthesize a second ligated product. The second ligated product has the following structure.

P5-A5-cDNA1-A3-A5-cDNA2-A3-A5-cDNA3-A3-A5-cDNA4-A3-P3

Here, the A3, A5, P3, and P5 are as defined above, and the cDNA1, cDNA2, cDNA3, and cDNA4 refer to one of the cDNAs complementary to SEQ ID NOS: 1 to 15.

A second ligated product including 4 cDNAs complementary to the target miRNA were synthesized (Bioneer Corporation, KOREA). 8 types of the second ligated products were prepared, using cDNAs of different targets. The cDNAs 1 to 4 of each of the eight ligated constructs are as provided in Table 2.

TABLE 2

| No. | cDNA1 | cDNA2 | cDNA3 | cDNA4 | GC content (%) |
|---|---|---|---|---|---|
| 1 | hsa-mir-16 | hsa-mir-3665 | hsa-mir-3196 | hsa-mir-1915 | 58.1 |
| 2 | hsa-mir-1307 | hsa-mir-1203 | hsa-mir-25 | hsa-mir-1 | 49.4 |
| 3 | hsa-mir-17 | hsa-mir-25 | hsa-mir-1307 | hsa-mir-1203 | 51.8 |
| 4 | hsa-mir-31 | hsa-mir-3141 | hsa-mir-25 | hsa-mir-16 | 49.1 |
| 5 | hsa-mir-2861 | hsa-mir-25 | hsa-mir-1307 | hsa-mir-95 | 52.1 |
| 6 | hsa-mir-1307 | hsa-mir-1203 | hsa-mir-7 | hsa-mir-9 | 48.4 |
| 7 | hsa-mir-1307 | hsa-mir-16 | hsa-mir-3196 | hsa-mir-31 | 53.2 |
| 8 | hsa-mir-1307 | hsa-mir-2861 | hsa-mir-31 | hsa-mir-3196 | 58.0 |

3. Amplification of Target Nucleic Acid

Target nucleic acids were amplified by PCR using the first ligated product and the second ligated product prepared as described above as templates. An oligonucleotide having a sequence of SEQ ID NO: 16 was used as a forward primer, and an oligonucleotide having a sequence of SEQ ID NO: 18 was used as a reverse primer. Quantitative real-time PCR (qRT-PCR) was performed, and the amplified products were identified in real time using a SYBR GREENI.

The qRT-PCR was performed 40 cycles using a Roche LC480 at 95° C. for 10 minutes, (at 95° C. 15 sec/at 55° C. 1 min), and a ramping rate was 3.3° C./sec. A PCR mixture for amplifying the first ligated product included 0.5 nM of each template cDNA, 500 nM of each of the forward and reverse primers, and a SYBR GREEN master mix (Universal RT, Exiqon, #203450). The SYBR GREEN master mix is a mixture including a DNA polymerase, a buffer, dNTP, and SYBR GREENI.

A PCR mixture for amplifying the second ligated product included 0.5 nM of each template cDNA, 500 nM of each of the forward and reverse primers, and a SYBR GREEN master mix (Universal RT, Exiqon, #203450). The SYBR GREEN master mix is a mixture including a DNA polymerase, a buffer, dNTP, and SYBR GREENI.

The amplified miRNA was determined by measuring a threshold cycle (Ct) value.

4. Amplification Results

The amplification results of the first ligated product are shown in Table 3 below as variance values (CV %) with respect to average Ct values.

TABLE 3

| 15 types of miRNAs | Average Ct (cycle) | 21.43 |
|---|---|---|
|  | CV (%) | 10.92 |
| miRNA having GC content in the range of 20 to 80% | Average Ct (cycle) | 20.73 |
|  | CV (%) | 5.83 |
| miRNA having GC content greater than 80% | Average Ct (cycle) | 23.37 |
|  | CV (%) | 16.03 |

As shown in Table 3, the Ct value varies according to the GC content of the target nucleic acid. While 11 types of miRNAs having the GC content in the range of 20 to 80% had an average Ct value of 20.73 and a variance value of 5.83%, 4 types of miRNAs (hsa-mir-1915, 2861, 3195, and 3196) having the GC content greater than 80% had an average Ct value of 23.37 and a variance value of 16.03% under the same experimental conditions. This indicates that the variance value increases as the GC content increase. That is, amplification bias exists according to the sequence of the target nucleic acid, i.e., the GC content.

The amplification results of the second ligated product are shown in Table 4 below.

TABLE 4

| No. | GC content (%) | Ct (cycle) |
|---|---|---|
| 1 | 58.1 | 20.23 |
| 2 | 49.4 | 18.40 |
| 3 | 51.8 | 20.67 |
| 4 | 49.1 | 21.57 |
| 5 | 52.1 | 19.08 |
| 6 | 48.4 | 20.56 |
| 7 | 53.2 | 21.25 |
| 8 | 58 | 21.81 |

When the second ligated product is amplified, miRNA had an average Ct value of 20.44 and a variance value of 5.83%, which indicate similarity to those of the first ligated product having the GC content in the range of 20 to 80%. This indicates that the amplification bias of each of the miRNAs generated by the base sequence difference including the GC content difference may be offset when the second ligated product is amplified.

Example 2

Ligation and Amplification of miRNA 8 types of miRNAs having different GC contents were selected as target nucleic acids to be amplified. The selected 8 types of miRNAs are listed in Table 5 below.

TABLE 5

| Name of miRNA | SEQ ID NO: | GC content | Tm | Length |
|---|---|---|---|---|
| 1 | hsa-mir-95 | 1 | 36.4 | 60 | 22 |
| 2 | hsa-mir-1307 | 10 | 72.7 | 76 | 22 |
| 3 | hsa-mir-1203 | 9 | 71.4 | 71.4 | 21 |
| 4 | hsa-mir-4271 | 19 | 63.2 | 62.0 | 19 |
| 5 | hsa-mir-1915 | 12 | 90 | 76 | 20 |
| 6 | hsa-mir-3141 | 11 | 73.7 | 66 | 19 |

TABLE 5-continued

| | Name of miRNA | SEQ ID NO: | GC content | Tm | Length |
|---|---|---|---|---|---|
| 7 | hsa-mir-2861 | 13 | 89.5 | 72 | 19 |
| 8 | hsa-mir-3665 | 15 | 83.3 | 66 | 18 |
| | Average | | 72.48 | | |
| | Standard deviation | | 17.28 | | |

In Table 5, miRNAs are synthesized miRNAs (Bioneer Corporation, KOREA) having a concentration of about 1 pmole/ul and a phosphorylated 5'-terminal and 3'-OH terminal and stored at −20° C. An adaptor sequences and/or a primer sequence are ligated to miRNA, and the ligated product was amplified. Sequences used in the ligation and amplification are as follows.

```
P5-A5:
                                    (SEQ ID NO: 20)
5'-CGGUGAGGUCUUUGGUUCAUCGAUCG-3'

A3-P3:
                                    (SEQ ID NO: 21)
5'-CGAUCGUGUCCUCAAGGCUACCACCU-3'

Reverse-transcribing primer:
                                    (SEQ ID NO: 22)
5'-ATCGCGAGAATTCCA-3'

Forward primer of PCR:
                                    (SEQ ID NO: 23)
5'-CGGTGAGGTCTTTGGTTCAT-3'

Reverse primer of PCR:
                                    (SEQ ID NO: 24)
5'-AGGTGGTAGCCTTGAGGACA-3'
```

P5-A5, A3-P3, primer of reverse-transcription, and primers of PCR were purchased from Bioneer Corporation (KOREA).

(1) Ligation of A3-P3 Sequence to 3'-Terminal 8 types of miRNAs listed in Table 5 were mixed such that the concentration of each miRNA was 1 pmole/ul, and 1 ul of the mixture was mixed with 1 ul of the A3-P3 (160 fmole/ul). Then, the mixture was added to a reaction buffer including 10 units of T4 RNA ligase (NEB, 1× T4 RNA ligase reaction buffer supplemented with 1 mM ATP), and RNA ligation was performed at 37° C. for 2 hours.

In this regard, a constant mass ratio of A3-P3 to the total miRNA was maintained such that about four miRNAs are randomly ligated in the 5'-direction where A3-P3 was ligated to the 3'-terminal (⅙ adaptor with respect to the total miRNA). The first ligated product prepared as described above may be miRNA-miRNA-A3-P3, miRNA-miRNA-miRNA-A3-P3, miRNA-miRNA-miRNA-miRNA-A3-P3, miRNA-miRNA-miRNA-miRNA-miRNA-A3-P3, miRNA-miRNA-miRNA-miRNA-miRNA-miRNA-A3-P3, or the like. The 3'-terminal of the A3-P3 was blocked with 3'-dideoxycytidine (3'-ddC).

(2) Ligation of P5-A5 to 5'-Terminal 1 ul of P5-A5 having a concentration of 10 pmole/ul was added to the reaction mixture prepared in operation (1) above, and the P5-A5 sequence was ligated to the 5'-terminal thereof in the same reaction condition as operation (1) above. As a result, sequences P5-A5-miRNA-miRNA-A3-P3, P5-A5-miRNA-miRNA-miRNA-A3-P3, P5-A5-miRNA-miRNA-miRNA-miRNA-A3-P3, P5-A5-miRNA-miRNA-miRNA-miRNA-miRNA-A3-P3, P5-A5-miRNA-miRNA-miRNA-miRNA-miRNA-miRNA-A3-P3, or the like (hereinafter, referred to as first ligated product) was prepared.

In addition, as a control group, -A3-P3 and P5-A5- were respectively ligated to the 3'-terminal and the 5'-terminal of each of the 8 types of miRNAs in the same manner as operations (1) and (2) to obtain P5-A5-miRNA-A3-P3.

(3) Reverse Transcription

Reverse transcriptions of the first ligated products of the experimental groups obtained in operation (2) above and the ligated product of the control group were performed using a reverse-transcription primer of SEQ ID NO: 22.

Reverse transcription was performed by incubating 1 ul (1 pmole/ul) of each sample of the experimental and control groups according to a protocol of TaqMan™ MicroRNA Reverse Transcription Kit (MultiScribe™ Reverse Transcriptase, 50 U/ul, Applied Bioscience; 4366596) at 16° C. for 30 minutes, at 42° C. for 30 minutes, and at 85° C. for 5 minutes. As a result, a cDNA product was obtained.

(4) Amplification and Result

Quantitative real-time PCR (qRT-PCR) was performed using the cDNA product obtained in operation (3) above as a template and respectively using 900 nM of sequences of SEQ ID NOS: 23 and 24 as a forward primer and a reverse primer. The qRT-PCR was performed by using an Applied Biosystems Taqman™ Universal PCR Master Mix II, No UNG (part number: #4440043) kit and 250 nM of a Taqman probe (customized by Applied Biosystems). The qRT-PCR was performed under conditions including denaturations at 95° C. for 10 minutes one time, and 45 times of denaturations at 95° C. for 10 seconds; and annealing and polymerization at 60° C. for 10 seconds. The amplified product was analyzed by electrophoresis by using a BioAnalyzer 2100 (Agilent).

FIGS. 1A and 1B show electrophoresis results of amplified products. FIG. 1A is a photograph of electrophoresis, and FIG. 1B is an electropherogram of FIG. 1A. In FIG. 1B, plot (a) shows an experimental group, plot (b) shows a control group, and peaks 3, 4, and 5, respectively, show a ligated product of one miRNA (about 74 bp), a ligated product of two miRNAs (about 94 bp), and a ligated product of five miRNAs (about 154 bp). As shown in FIG. 1B, the production of by-products was reduced in the experimental group compared with the control group, since -A3-P3 was not excessively used. In FIG. 1A, M indicates molecular size marker, lane 1 indicates experimental group (ligated product) and lane 2 indicates a control group (no ligated reaction). In FIG. 1B, x axis indicates Labchip running time (sec) and y axis is fluorescent intensity (arbitrary unit).

Thus, as shown in FIG. 1B, it was identified that the first ligated product including four to five miRNAs on average was prepared in the experimental groups. In Example 2, the experiment was performed in condition where four to five miRNAs may be ligated.

Since the length of -A3-P3 or P5-A5- is 26 nt, and the length of miRNA is in the range of 18 to 22 nt, a ligated product of -A3-P3 or P5-A5- and one miRNA has a length of about 70 to about 74 nt, a ligated product of -A3-P3 or P5-A5- and two miRNAs has a length of about 88 to about 96 nt, a ligated product of -A3-P3 or P5-A5- and three miRNAs has a length of about 106 to about 118 nt, a ligated product of -A3-P3 or P5-A5- and four miRNAs has a length of about 124 to about 140 nt, and a ligated product of -A3-P3 or P5-A5- and five miRNAs has a length of about 142 to about 162 nt.

Since the ligation randomly occurs, various ligated products having different lengths as described above may be obtained. However, the size distribution depends on an initial amount of -A3-P3. For example, since both of miRNA and -A3-P3 are involved in the ligation, if the ratio of the total amount of miRNAs to the amount of -A3-P3 is 1:1, it is anticipated that the ligation occurs such that the ratio of the ligated product is 1:1. When the amount of -A3-P3 is ⅙ of that of the total miRNAs, one -A3-P3 may be ligated to a ligated product of randomly selected five to six miRNAs. In addition, since the 3'-terminal of the -A3-P3 is blocked by dideoxycytidine (3'-ddC), the 3'-terminal of the -A3-P3 cannot be used for the ligation, so that the reaction of the 3'-terminal is terminated. Thus, when all of the -A3-P3s participate in the ligation, the ligation is terminated because there is no more 3'-terminal OH group to be used for the ligation with the 5'-terminal P group. However, this is not limited to a specific mechanism.

Table 6 shows the results of qRT-PCR of the experimental groups and the control group using ΔCt values.

TABLE 6

| No. | Name of miRNA | Control group (ΔCt) | Experimental group (ΔCt) |
|---|---|---|---|
| 1 | hsa-mir-95 | 2.912 | 0.995 |
| 2 | hsa-mir-1203 | −1.218 | 0.245 |
| 3 | hsa-mir-1307 | 1.812 | 0.695 |
| 4 | hsa-mir-1915 | −0.198 | −0.035 |
| 5 | hsa-mir-2861 | −2.128 | −0.765 |
| 6 | hsa-mir-3141 | 1.422 | −0.205 |
| 7 | hsa-mir-3665 | −1.998 | −0.945 |
| 8 | hsa-mir-4271 | −0.608 | 0.015 |
| | max − min of ΔCt | 5.04 | 1.94 |

The Ct value of each experimental group (8 groups) was measured using a device, and the ΔCt was calculated by subtracting a Ct value of each miRNA from an average Ct value of the 8 experimental groups. Thus, the ΔCt of the control group is calculated by subtracting each Ct value from the average Ct value of the control group, and the ΔCt of the experimental group is calculated by subtracting each Ct value from the average Ct value of the experimental group, where deviation with respect to the average value is shown. The max-min of ΔCt is a difference between miRNA having the highest ΔCt value and miRNA having the lowest ΔCt value in the control group and the experimental groups. Theoretically, the efficiency of the miRNA amplification is the same if the max-min of ΔCt is 0, and the difference of the amount of the amplified miRNA is about 10 times if the difference of the max-min of ΔCt is 3.3.

As shown in Table 6, the max-min of ΔCt of the control group was 5.04 even though the same amount of miRNA was used. This indicates that the expressed amount of each miRNA varies by 32.9 times. On the other hand, the max-min of ΔCt of the experimental groups was 1.94. This indicates that the expressed amount of each miRNA varies by 3.8 times. That is, an amplification variation (bias) of the experimental groups was reduced to 1/10 of that of the control group.

According to these results, the amplification bias may be reduced by ligating a plurality of miRNAs and then amplifying the ligated product.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of simultaneously amplifying a plurality of target nucleic acids, the method comprising:
providing a biological sample comprising a plurality of target nucleic acids, wherein the target nucleic acids are miRNA;
ligating two or more different target nucleic acids from the biological sample, or cDNA synthesized therefrom, to provide a ligated product; and
amplifying the ligated product.

2. The method of claim 1, wherein the ligating is performed using an RNA ligase or a DNA ligase.

3. The method of claim 1, wherein ligating two or more target nucleic acids comprises introducing an adaptor sequence between the target nucleic acids, an adaptor sequence at 5'-terminal of a target nucleic acid, an adaptor sequence at 3'-terminal of a target nucleic acid, or a combination thereof.

4. The method of claim 1, wherein the method comprises providing at least one target nucleic acid comprising a 3'-terminal adaptor sequence, and at least one target nucleic acid comprising a 5'-terminal adaptor sequence, and ligating the 3'-terminal adapter sequence of one nucleic acid to the 5'-adapter sequence of the other nucleic acid.

5. The method of claim 1, further comprising ligating a primer sequence or a primer-binding sequence, to at least one of the 3'-terminal or the 5'-terminal of the ligated product.

6. The method of claim 1, wherein each target nucleic acid has a length of about 200 nt or less.

7. The method of claim 1, wherein each target nucleic acid has a length in the range of about 18 to about 30 nt.

8. The method of claim 1, wherein the ligated product is amplified as a single transcript.

9. The method of claim 1, wherein the method comprises reverse-transcribing two or more target miRNA molecules from the biological sample to provide cDNA molecules, and ligating the cDNA molecules to provide the ligated product.

10. The method of claim 1, wherein the method comprises ligating two or more different target miRNA molecules to provide a ligated miRNA product and reverse-transcribing the ligated miRNA product to provide a ligated cDNA product.

11. The method of claim 9, further comprising ligating an adaptor sequence to at least one of the 3'-terminal and the 5'-terminal of each target miRNA molecules before reverse-transcribing the target miRNA molecules.

12. The method of claim 9, further comprising ligating an adaptor sequence to at least one of the 3'-terminal and the 5'-terminal of the cDNA molecules after reverse-transcribing the target miRNA molecules.

13. The method of claim 1, wherein amplifying is performed by PCR, and forward and reverse primers are specifically annealed to a primer binding region of the ligated product that is separate from a target nucleic acid sequence.

14. A method of determining a relative amount of a target nucleic acid in a sample, the method comprising:
amplifying two or more target nucleic acids contained in a biological sample according to the method of claim 1, wherein the target nucleic acids comprise miRNA;
measuring the amount of each target nucleic acid from the amplified product; and
determining a relative amount of the target nucleic acid in the sample by using the measured amount.

15. The method of claim 1, wherein ligating two or more target nucleic acids, or cDNA synthesized therefrom, comprises combining two or more different target nucleic acids with one or more 3'-adapter sequences, one or more 5'-adapter sequences, and a nucleic acid ligase.

16. The method of claim 1, wherein ligating two or more target nucleic acids, or cDNA synthesized therefrom, comprises combining two or more different target nucleic acids with one or more pre-ligated, end-blocked 3'-primer-adapter sequences, or one or more pre-ligated, end-blocked 5'-primer-adapter sequences.

17. The method of claim 1, wherein the GC content of the ligated product is about 20-80%.

18. The method of claim 1, wherein amplification of the ligated product results in a copy number of each of the ligated target nucleic acids that is proportional to the relative abundance of the target nucleic acids in the biological sample with reduced amplification bias as compared to amplification of the target nucleic acids without ligation to provide a ligated product.

19. The method of claim 1, wherein the method comprises ligating 5 or more different target nucleic acids from the biological sample, or cDNA synthesized therefrom, to provide a ligated product.

* * * * *